(12) United States Patent  (10) Patent No.: US 9,315,890 B1
Frick et al.  (45) Date of Patent: Apr. 19, 2016

(54) SYSTEM AND METHOD FOR VOLATILIZING ORGANIC COMPOUNDS

(76) Inventors: Markus Frick, Reno, NV (US);
Richard Hicksted, Reno, NV (US)

( * ) Notice: Subject to any disclaimer, the term of this patent is extended or adjusted under 35 U.S.C. 154(b) by 1031 days.

(21) Appl. No.: 12/950,917

(22) Filed: Nov. 19, 2010

(51) Int. Cl.
*A24F 47/00* (2006.01)
*C23C 14/26* (2006.01)
*A61L 9/03* (2006.01)
*C23C 16/448* (2006.01)

(52) U.S. Cl.
CPC . *C23C 14/26* (2013.01); *A61L 9/03* (2013.01); *C23C 16/4481* (2013.01)

(58) Field of Classification Search
CPC . A61M 11/00; A61M 11/005; A61M 11/042; A61M 15/0003; A61M 15/0065; A61M 15/0083; A61M 15/06; A61M 16/00; A24F 47/008; A61L 9/03; C23C 14/26; C23C 16/4481
USPC ........... 219/488; 128/203.26, 203.27, 200.14, 128/200.21, 204.14, 204.17, 200.11, 128/200.24, 202.21, 203.12, 203.15, 128/203.16, 203.17; 392/386, 387, 390, 392/397
See application file for complete search history.

(56) References Cited

U.S. PATENT DOCUMENTS

| | | | |
|---|---|---|---|
| 6,766,220 B2 * | 7/2004 | McRae et al. | 700/266 |
| 6,772,756 B2 * | 8/2004 | Shayan | 128/203.26 |
| 6,990,978 B2 | 1/2006 | Shayan | |
| 7,622,140 B2 | 11/2009 | Whittle et al. | |
| 8,483,552 B2 * | 7/2013 | Durisek | 392/386 |
| 8,794,231 B2 * | 8/2014 | Thorens et al. | 128/202.21 |
| 2005/0185392 A1 * | 8/2005 | Walter et al. | 362/96 |
| 2006/0196518 A1 * | 9/2006 | Hon | 131/360 |
| 2006/0283449 A1 | 12/2006 | Balch et al. | |
| 2008/0023003 A1 * | 1/2008 | Rosenthal | 128/203.26 |
| 2008/0092913 A1 * | 4/2008 | Sugai et al. | 132/53 |
| 2008/0142010 A1 * | 6/2008 | Weaver et al. | 128/203.26 |
| 2009/0078253 A1 | 3/2009 | Bao | |
| 2009/0095311 A1 * | 4/2009 | Han | 131/194 |
| 2009/0126745 A1 * | 5/2009 | Hon | 131/273 |
| 2009/0283103 A1 * | 11/2009 | Nielsen et al. | 131/273 |
| 2010/0043809 A1 | 2/2010 | Magnon | |
| 2010/0242974 A1 * | 9/2010 | Pan | 131/273 |
| 2011/0277780 A1 * | 11/2011 | Terry et al. | 131/273 |

OTHER PUBLICATIONS

Wikipedia. "Vaporizer". http://en.wikipedia.org/wiki/Vaporizer . Aug. 4, 2010.

(Continued)

*Primary Examiner* — Dana Ross
*Assistant Examiner* — James Sims, III
(74) *Attorney, Agent, or Firm* — Kerr IP Group, LLC; Michael A. Kerr

(57) ABSTRACT

An electronic device for volatilizing organic matter is described. The electronic device includes a housing, a removable transparent tube, a heating element, a setting profile, a memory and a processor. The removable transparent tube has a chamber distal end within the housing. The heating element is proximate to the chamber distal end of the transparent tube. The chamber distal end holds vaporizable organic matter. The settings profile includes a first wattage setting and a first timer setting for the heating element and the heating element vaporizes the vaporizable material. The memory stores the settings profile. The processor is operatively coupled to the memory module and controls the heating element according to the settings profile.

20 Claims, 10 Drawing Sheets

(56) References Cited

OTHER PUBLICATIONS

K.J. Rockwise. "Fuck Combustion: The Oracle Vaporizer". http://www.fuckcombustion.com/viewtopic.php?id=2269&p=1 . Oct. 1, 2010.

Ian'S Brain, Busted Neurons. "Advantages and types of marijuana vaporizers—Cannabis vaporizers: a safer alternative". http://iansbrain.com/advantages-and-types-of-marijuana-vaporizers/ . Feb. 8, 2009.

* cited by examiner

SYSTEM AND METHOD FOR VOLATILIZING ORGANIC COMPOUNDS

FIELD OF THE INVENTION

The present invention relates to a system and method for volatilizing organic compounds. More specifically, the invention relates to a device for volatilizing organic compounds that includes a heating element.

BACKGROUND

Vaporizers provide an alternative to smoking for the delivery of medicinal, therapeutic, aromatic or psychoactive materials. Generally, a vaporizer heats plant material so that the active compound is delivered as a vapor for inhalation. The vapor produced by the vaporization lacks the potentially harmful combustion byproducts that may be inhaled when the material undergoes a combustion or conduction process, i.e. the material is smoked.

Many currently available vaporizers are powered by electrical outlets or large batteries that diminish the portability of the device Vaporizers designed for portability may require butane fuel cartridges which require replacement. It may be undesirable to transport butane due to its combustible nature. Other portable vaporizers require a long period of time for the heating element to reach a temperature required to vaporize the desired active compound. Thus, there remains a need for a rechargeable portable vaporizer capable of rapid heating.

Typically, vaporizers require a large amount of power to achieve the temperature required for vaporization by conduction heating or to heat a volume of air for convection heating. The power requirements diminish the portability of the vaporizers. It would thus be desirable to have a portable vaporizer that more efficiently vaporizes organic compounds.

Additionally, there are limitations associated with inhalation-based drug delivery systems such as metered dose inhalers and dry powder inhalers. Metered dose inhalers require coordination between actuation of the device and inhalation, which is problematic for many users. Particles produced by dry particle inhalers may be too large to penetrate the lungs. Thus, there is a need for a portable vaporizer capable of delivering therapeutic compounds for inhalation.

SUMMARY

A device for volatilizing organic matter is described. The device includes a housing, a removable transparent tube, a heating element and a removable heat shield. The removable transparent tube has a chamber distal end within the housing. The heating element is proximate to the chamber distal end of the transparent tube. The chamber distal end holds a vaporizable organic matter. The removable heat shield is coupled to the housing at the distal end of the housing.

An electronic device for volatilizing organic matter is also described. The electronic device includes a housing, a removable transparent tube, a heating element, a setting profile, a memory and a processor. The removable transparent tube has a chamber distal end within the housing. The heating element is proximate to the chamber distal end of the transparent tube. The chamber distal end holds vaporizable organic matter. The settings profile includes a first wattage setting and a first timer setting for the heating element and the heating element vaporizes the vaporizable material. The memory stores the settings profile. The processor is operatively coupled to the memory module and controls the heating element according to the settings profile.

An electronic device for volatilizing organic compounds is also described. The electronic device includes a heating element, a settings profile, a memory, a processor, a power supply and a user switch. The heating element is proximate to a vaporization chamber. The settings profile includes a first wattage setting and a first timer setting for the heating element. The heating element volatilizes at least one active compound in the chamber. The memory stores the settings profile. The processor is operatively coupled to the memory module and receives the settings profile. The processor also controls the heating element according to the settings profile. The power supply is also controlled by the processor. The user switch is communicatively coupled to the processor. The user switch activates the heating element according to the settings profile to volatilize the active compound in the chamber.

A method of volatilizing organic compounds with an electronic device is described. The method includes storing a settings profile in a memory. The method proceeds to activate the heating element with a user switch. The setting profile is then initiated and the heating element is powered. The activation of the heating element is controlled according to the settings profile with a processor. At least one active compound in the chamber is volatilized.

A portable device for vaporizing matter is also described. The portable device comprises a first insulating tube and a second insulating tube disposed around the first insulating tube. A resistance wire is coiled around the second insulating tube. At least one wire terminal is coupled to the resistance wire. A processor directs the supply of power from at least one battery to the at least one wire terminal. Vaporizable matter is trapped between the first screen and the second screen within the first insulating tube.

In another embodiment, a portable device for vaporizing matter comprises a first insulating tube and a second insulating tube disposed around the first insulating tube. The portable device further comprises a means for generating an electromagnetic wave. A processor directs the supply of power from at least one battery to the means for generating an electromagnetic wave. Vaporizable matter is trapped between the first screen and the second screen within the first insulating tube.

A method for vaporizing matter in a portable device is also described. The method comprises trapping a vaporizable material between a first screen and a second screen within a first insulating tube. A processor directs a supply of power from at least one battery to at least one wire terminal. The at least one wire terminal is coupled to a wire terminal coupled to a resistance wire disposed around the first insulating tube. Infrared emissions from the resistance wire vaporize the vaporizable matter.

In a further embodiment, a portable system for vaporizing an active compound is described. The portable vaporization system comprises a tablet that includes a binder and the active compound. A vaporization chamber is configured to receive the binder and the active compound. A heating element is located proximate to the vaporization chamber. A processor is configured to process a plurality of instructions that control the heating element. The active compound is volatilized in the vaporization chamber when the heating element is activated by the processor.

DRAWINGS

The present invention will be more fully understood by reference to the following drawings which are for illustrative, not limiting, purposes.

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the apparatus and systems described herein may vary as to configuration and as to details. Additionally, the methods may vary as to details, order of the actions, or other variations without departing from the illustrative method disclosed herein.

A vaporizer applies heat to matter such that the active compounds are volatilized into an inhalable or aromatic vapor. Examples of organic plant matter used in vaporizers include Aloe vera, cannabis, chamomile, clove, coffee, eucalyptus, hops, gingko, lemon balm, sage, tea, thyme, and tobacco. Other organic compounds that are inhalable include therapeutic compounds such as medication, supplements, or vitamins. An inhalable therapeutic treatment may be fabricated for vaporization as a solid preparation of the medication or suspended in or applied to a material. Vaporizable matter as used herein refers to any therapeutic or plant matter volatilized to release therapeutic, aromatic or psychoactive compounds for inhalation.

A device for volatilizing organic matter is described. The device includes a housing, a removable transparent tube, a heating element and a removable heat shield. The illustrative device presented herein is a portable device and is shown in FIG. 1 through FIG. 6.

More generally, the removable transparent tube has a chamber distal end within the housing. The chamber distal end includes a wire screen that receives the vaporizable material, i.e. the organic matter that is subsequently volatilized. The heating element is proximate to the chamber distal end of the transparent tube. In one embodiment, the transparent tube has insulating properties resulting in an insulating tube. An illustrative transparent insulating tube is a quartz tube. The chamber distal end of the transparent tube holds a vaporizable organic matter. The chamber distal end also includes wire screen that receives the vaporizable organic material. The removable heat shield is coupled to the housing at the distal end of the housing. The removable heat shield includes a reflective shield and an end plate that covers the chamber distal end. A locking mechanism couples the heat shield to the housing.

Figure 7:
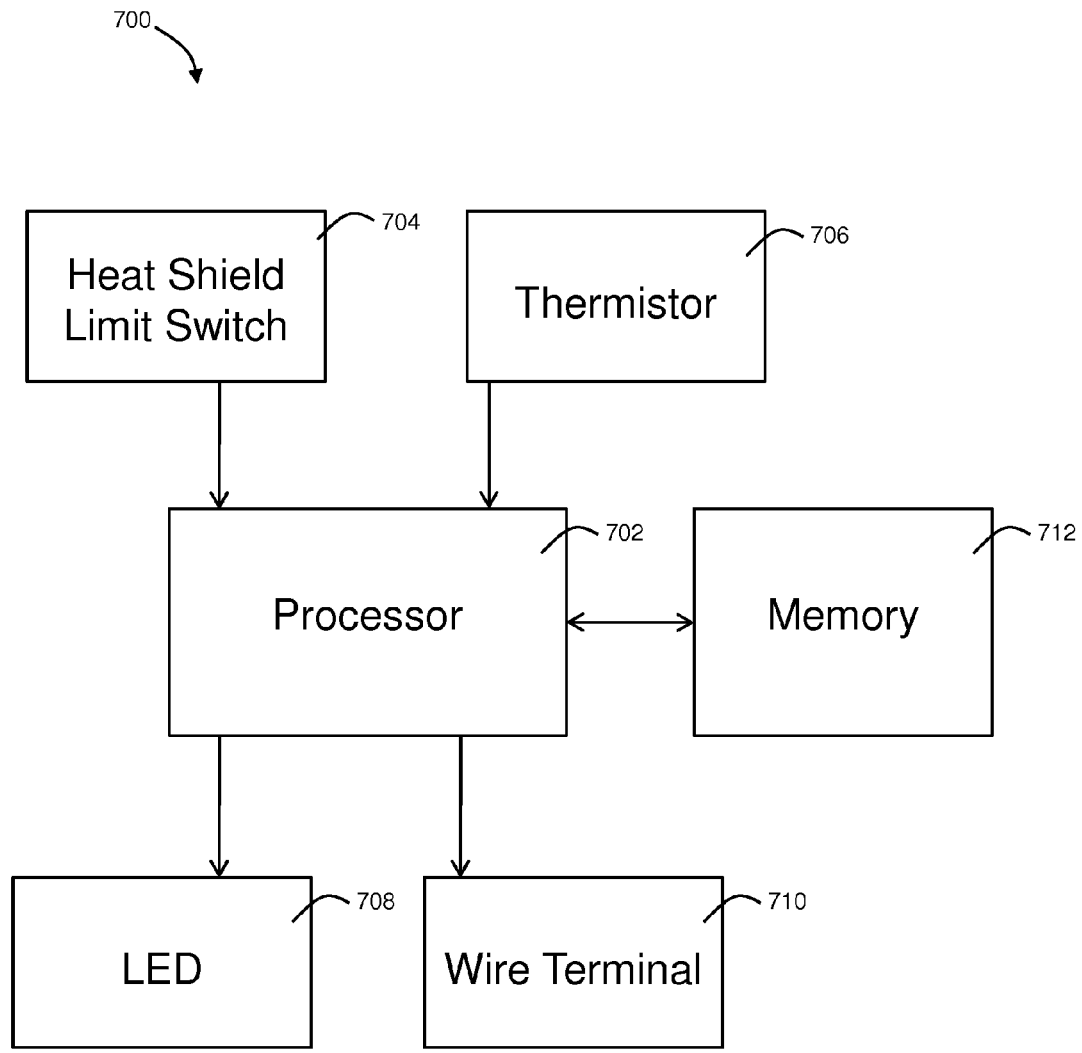
FIG. 7 shows an illustrative schematic diagram of a control system for the portable vaporizer.
Figure 8:
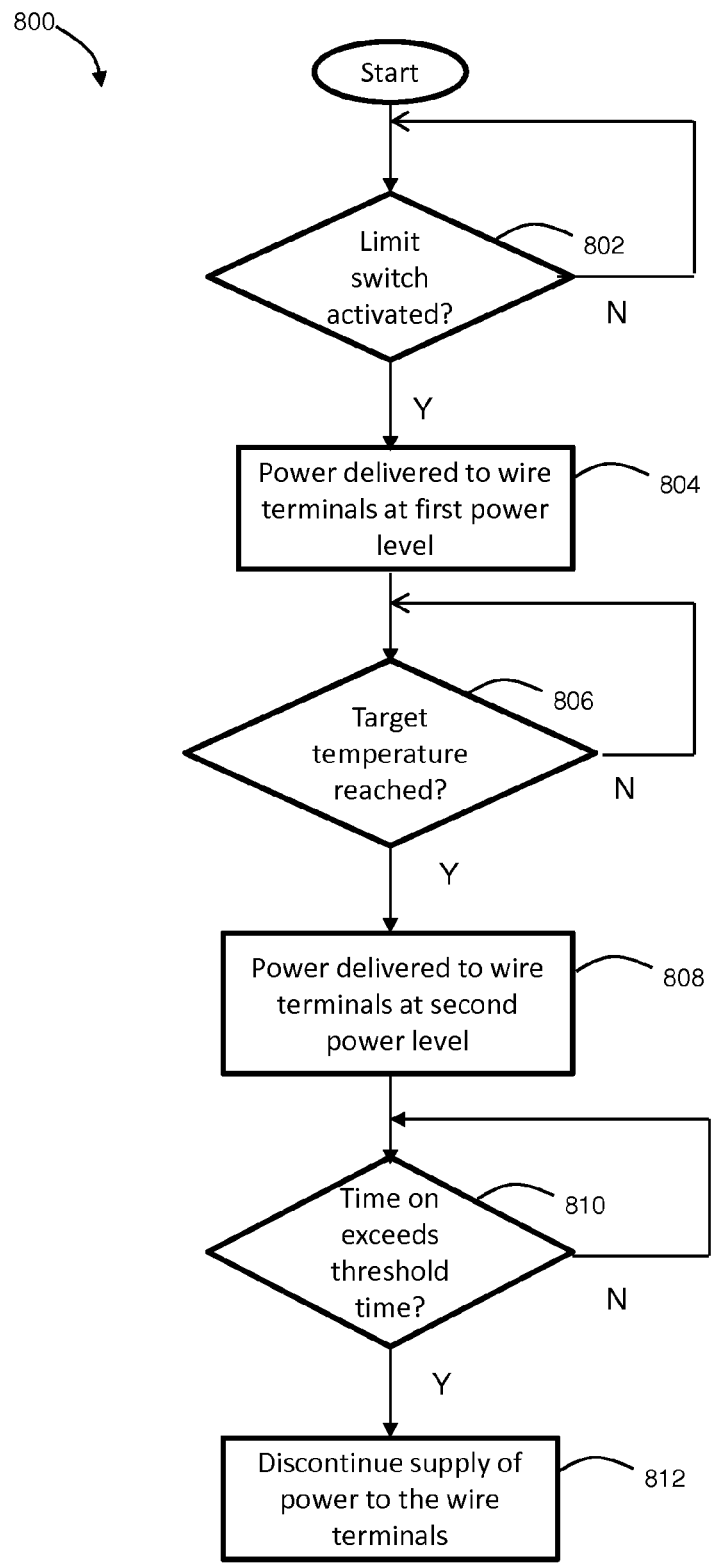
FIG. 8 shows an illustrative flowchart for controlling the portable vaporizer.
Figure 9:
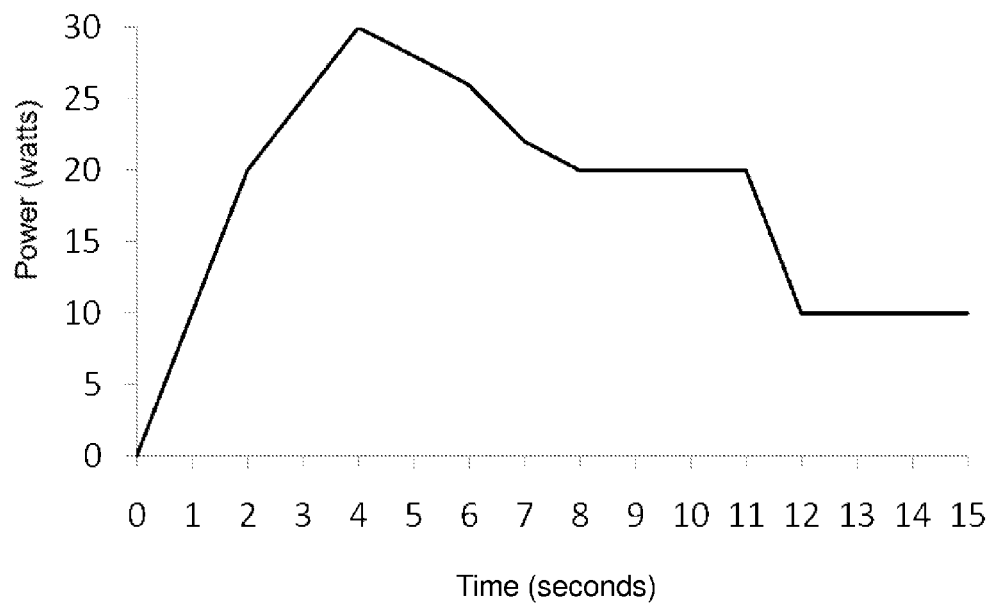
FIG. 9 shows an illustrative signal profile for a portable vaporizer.

In FIGS. 7-9, the systems and methods for operating the vaporizing device are presented. More generally, the illustrative vaporizing device also includes a settings profile with a first wattage setting and a first timer setting for the heating element. The settings profile is stored in a memory. A processor is coupled to the memory module and controls the heating element according to the settings profile. The heating element volatilizes at least one active compound in the chamber. A power supply is controlled by the processor. A user switch is also communicatively coupled to the processor. When the user switch is enabled, the heating element is activated according to the setting profile and volatilizes the active compound in the chamber.

In one embodiment, the heating element comprises a coiled resistance wire that operates as an infrared emitter that emits infrared energy at an electromagnetic frequency range between 1000 nm-20,000 nm. In an alternative embodiment, the heating element includes an ultraviolet emitter.

The electronic device also includes a control interface that is communicatively coupled to the processor and the memory. The control interface communicates one or more settings profiles that may be received from a personal computer that is communicatively coupled to a Wide Area Network such as the Internet. In the illustrative embodiment, the power supply for the electronic vaporizer also includes a rechargeable battery such as a lithium battery. The rechargeable battery is recharged with a power interface disposed on the electronic device. The heating element may be powered using AC power, DC power or any combination thereof. A calibration module calibrates the power output to the heating element. The control interface and power interface can be combined in a single I/O interface that is selected from the input/output (I/O) port group that includes USB, Firewire, ilink, Lynx and a DC power converter.

Additionally, a light indicator corresponding to the electronic device is activated according to one or more operational modes that includes a maximum operational time for the wattage setting. The light indicator may also be triggered by a battery voltage monitoring module that activates the light indicator when the rechargeable battery requires a recharge.

A method of volatilizing organic compounds with an electronic device is also described. The method includes storing a settings profile in a memory. The method activates the heating element with a user switch. The setting profile is then initiated and the heating element is powered. By way of example and not of limitation, the heating element comprises a resistance coil that emits infrared energy at an electromagnetic frequency range between 1000 nm-20,000 nm.

Additionally, other settings profiles may be communicated to the processor using a control interface. For the rechargeable battery embodiment, the power interface may use the same I/O port as used for the control interface. Each of the different settings provided include an operational mode with a maximum operational time and corresponding wattage settings.

The activation of the heating element is controlled according to the settings profile with a processor. At least one active compound in the chamber is volatilized. For the rechargeable battery embodiment, the available power from the rechargeable battery is monitored and when the available power falls below a threshold, an indicator is engaged that informs the user that the rechargeable battery requires recharging.

The illustrative electronic device described herein in further detail is a portable vaporizer that uses a resistance wire coil or other electromagnetic emitter to heat the contents of a transparent insulating tube such as a quartz tube. A second transparent insulating tube disposed around the first transparent insulating tube remains fixedly coupled. The second transparent insulating tube performs a variety of function including, but not limited to, protecting the resistance wire coil from being touched inadvertently by the user or from the removable tube that holds the illustrative plant matter.

Figure 1A:
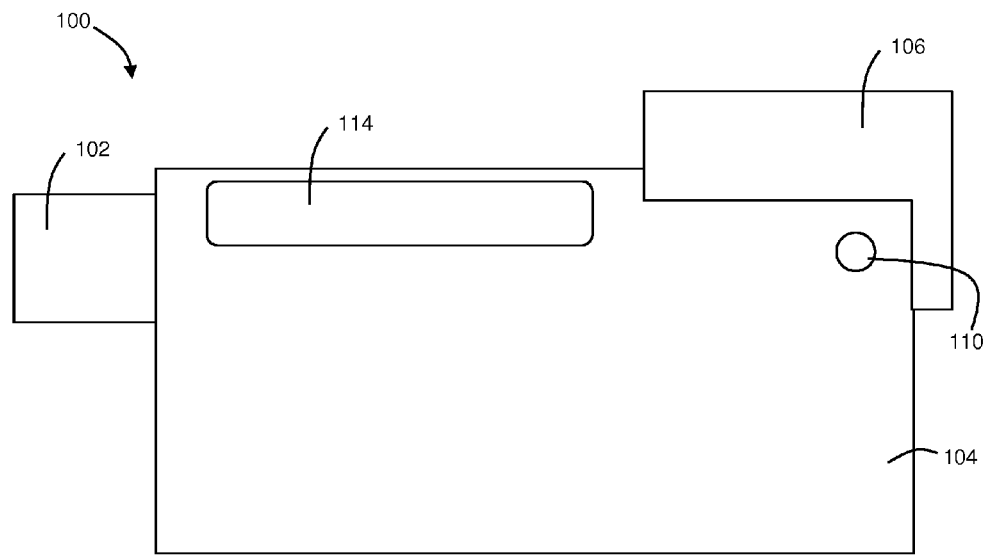
FIG. 1A shows an illustrative side elevation view of a portable vaporizer.

Referring to FIG. 1A, there is shown an illustrative elevation view of a portable vaporizer device 100. Inner transparent insulating tube 102 is seated in vaporizer housing 104. The vaporizer housing is preferably fabricated from a lightweight material such as aluminum. The inner transparent insulating tube is fabricated of an insulating material such as quartz. More generally, the inner tube touches the mouth of the user when the user inhales the vapor. Thus, the inner tube should have minimal conductive properties so heat from the heating element is not transferred to the open end of the inner tube that is used for inhaling.

The vaporizable matter is inserted into inner transparent insulating tube and secured between two screens as described in more detail with reference to FIG. 3. Removable heat shield 106 may be removed from the housing to allow insertion of vaporizable material within inner transparent insulating tube 102. The heat shield is fabricated from a material having high thermal conductivity, such as stainless steel or copper.

Figure 1B:
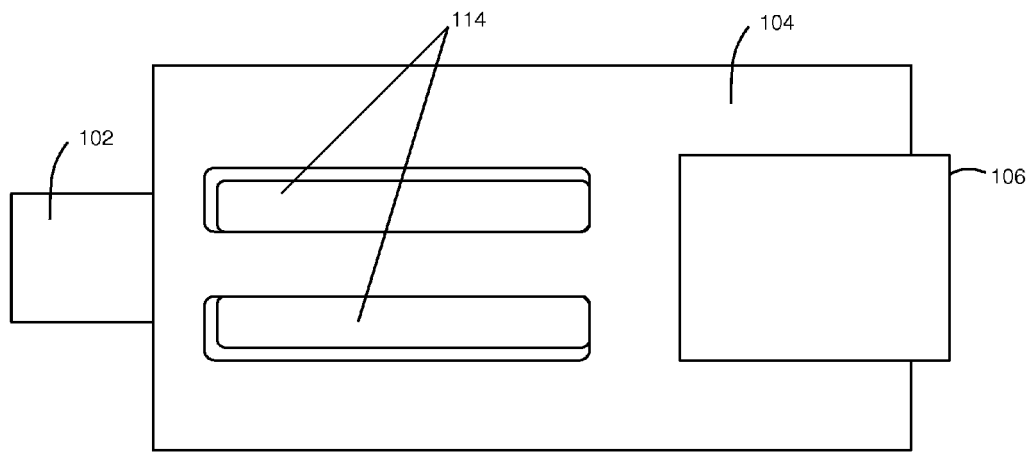
FIG. 1B shows an illustrative top view of a portable vaporizer.

The vaporizer may comprise spring loaded ball detent 110 configured to secure heat shield 106 in place within housing 104 when the heat shield has been fully inserted into the housing. The vaporizer housing may further include one or more slots 114. The slots are cutouts in the housing allowing vapor produced within inner transparent insulating tube 102 to be viewed. The vaporizer device may include LEDs configured to illuminate inner transparent insulating tube 102 when the LEDs are lit, such that the illuminated cylinder is visible through slots 114. FIG. 1B shows an illustrative top view of the portable vaporizing device.

Figure 2A:
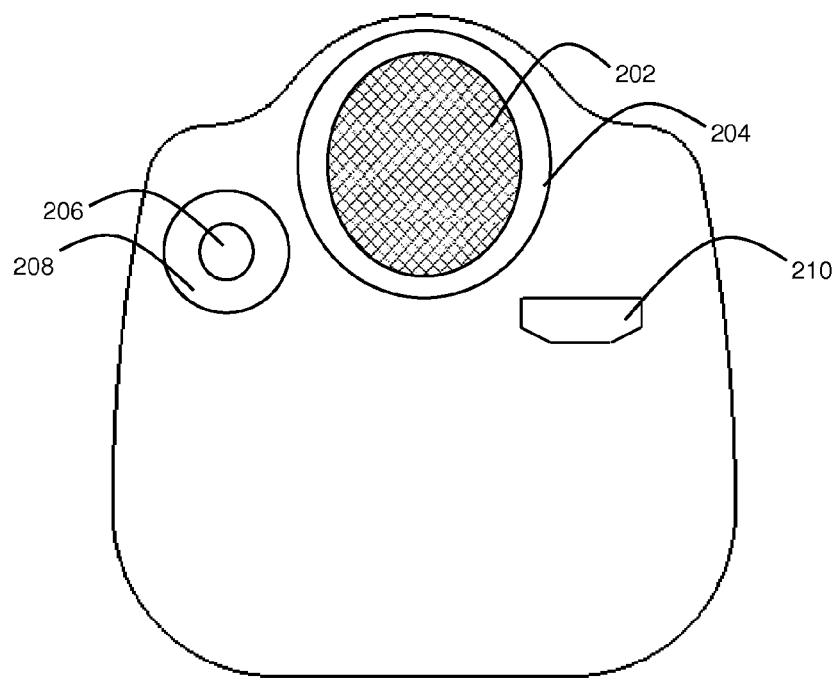
FIG. 2A shows an illustrative front elevation view of a portable vaporizer.

Referring to FIG. 2A, an illustrative front elevation view of the portable vaporizing device is shown. Front screen 202 is visible within inner transparent insulating tube 204. The vaporizing device comprises power switch 206 which may be located in a recessed area 208 of the housing as shown. Locating the power switch within the recessed area aids in the prevention of accidental activation of the power switch. The portable vaporizing device may comprise charging port 210 seated in the device housing. The charging port is any interface admitting a power source connector for recharging of the device batteries. The charging port may additionally serve as an interface for a data connection. For example, the charging port may be a Universal Serial Bus (USB) interface, such as a type Mini-A USB interface. Other illustrative charging ports include, but are not limited to, Firewire, ilink, Lynx and a DC power converter.

Figure 2B:
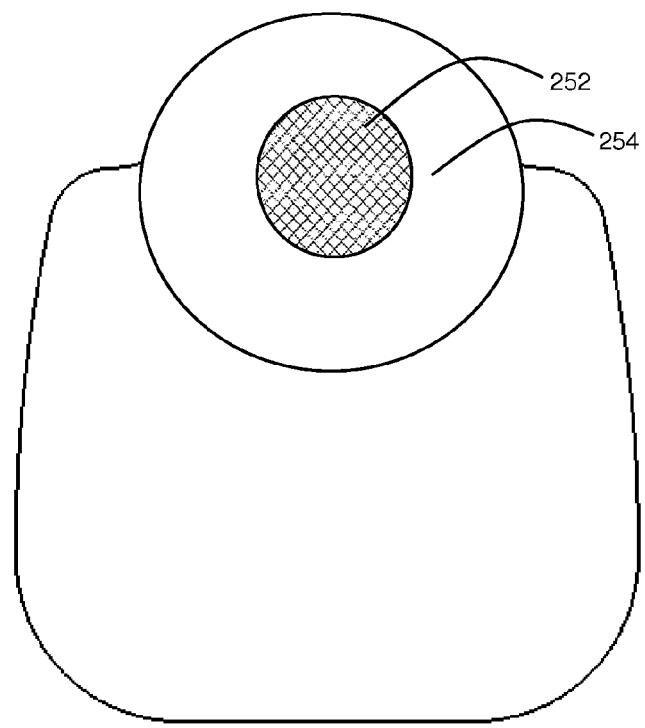
FIG. 2B shows an illustrative rear elevation view of a portable vaporizer.

Referring now to FIG. 2B, an illustrative rear elevation view of the portable vaporizing device is shown. In FIG. 2B, the rear screen 252 is visible beyond heat shield 254. The rear screen allows the organic compound in the vaporizing chamber to be mixed by the easier by either blowing out (exhaling) into the inner tube or by rotating the inner tube. The user may choose to mix the organic plant matter to improve vaporization by the heating element.

Figure 3:
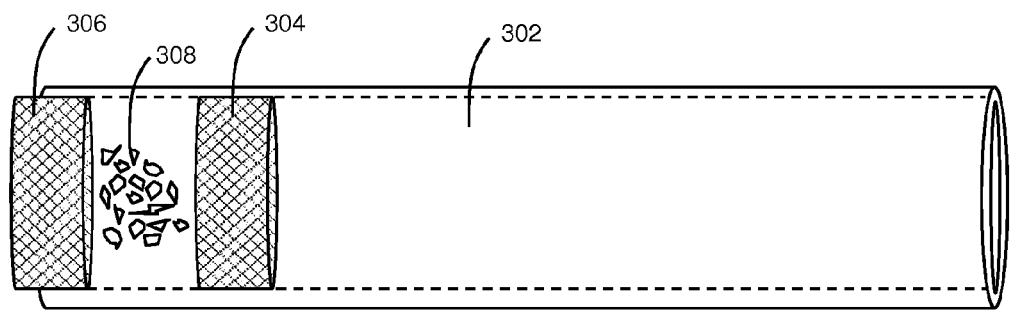
FIG. 3 shows an illustrative cross sectional view of an inner insulating tube of the portable vaporizer.

Referring to FIG. 3, an illustrative cross sectional view of inner transparent insulating tube 302 is shown. A front screen 304 and a rear screen 306 are shown inserted in the inner transparent insulating tube. The screens may be fabricated from a perforated material or wire mesh. In the illustrative example, each screen is formed from stainless steel wire mesh having a mesh/inch of 60×60 to 80×80. Each screen may be formed into a cup shape as shown at 304 and 306. To insert vaporizable matter 308 into the inner transparent insulating tube, rear screen 306 is removed and the matter is inserted into the tube. The rear screen is subsequently replaced, trapping the vaporizable matter 308 between the front screen 304 and rear screen 306. The area within the inner transparent insulating tube between the front screen and the rear screen may be referred to as the vaporization chamber. Front screen 304 may also be removable to allow cleaning and replacement of the screen.

Figure 4A:
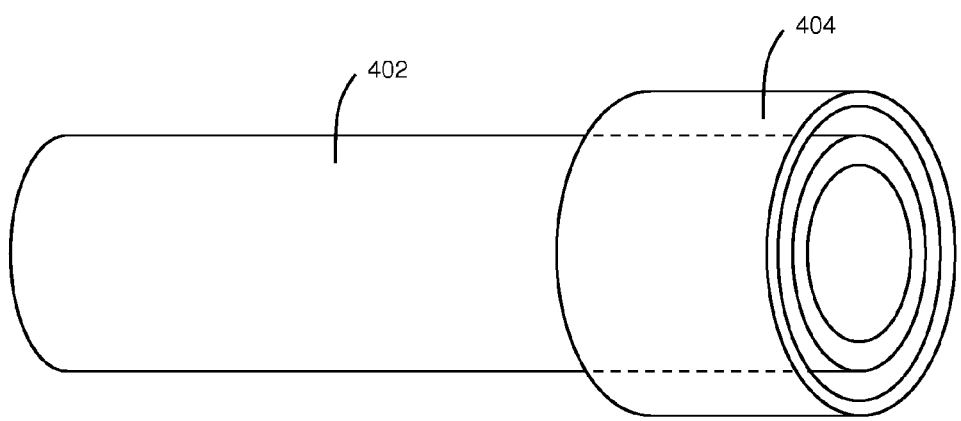
FIG. 4A shows an illustrative insulating tube assembly of the portable vaporizer.

Referring to FIG. 4A, the transparent insulating tube assembly of the portable vaporizing device is shown. The transparent insulating tube assembly comprises an inner transparent insulating tube 402 and an outer transparent insulating tube 404. Both transparent insulating tubes are fabricated from a thermally insulating material such as quartz. Outer transparent insulating tube 404 is received by a seat (not shown) built into the vaporizer housing.

Figure 4B:
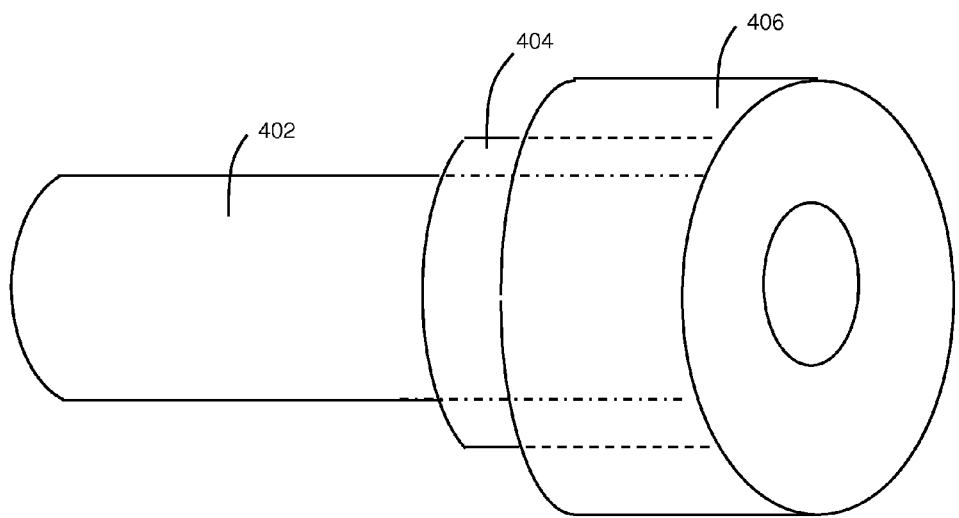
FIG. 4B shows the insulating tube assembly with heat shield.

FIG. 4B shows the transparent insulating tube assembly with heat shield. The heat shield 406 is shown disposed around outer transparent insulating tube 404. When fully disposed around the outer transparent insulating tube, the heat shield may secure rear screen 306 in place within inner transparent insulating tube 402.

Figure 4C:
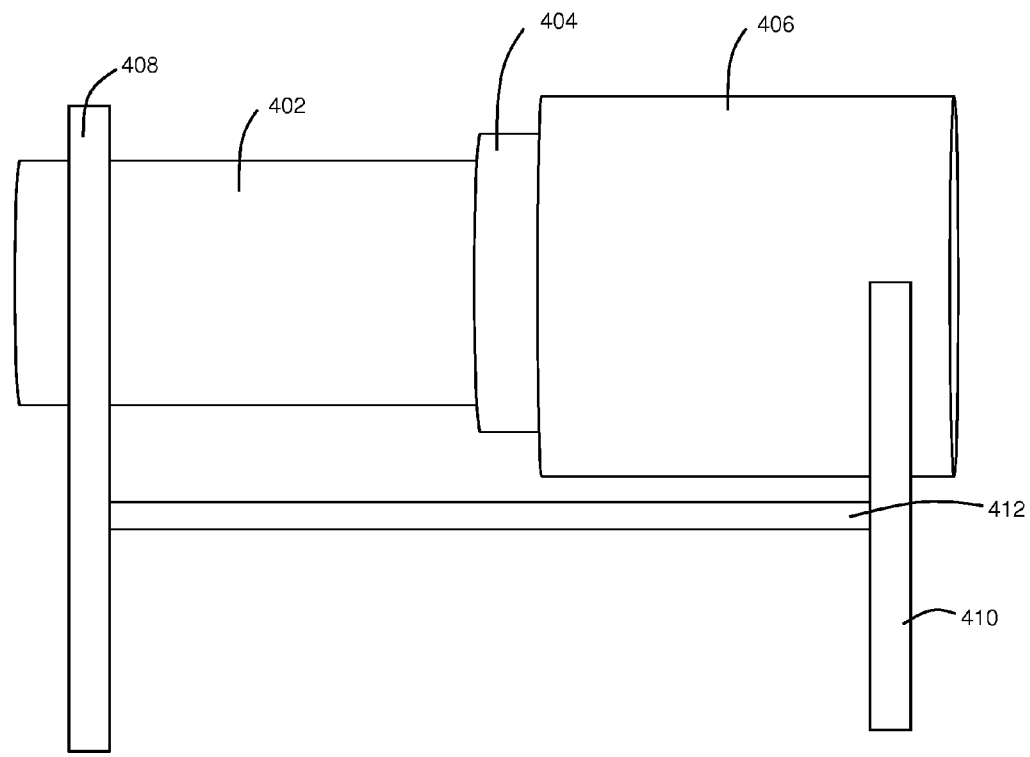
FIG. 4C shows the insulating tube assembly with heat shield as mounted relative to front and rear housing plates.

FIG. 4C shows the transparent insulating tube assembly with heat shield as mounted relative to front housing plate 408 and rear housing plate 410. Printed circuit board (PCB) 412 may also be mounted to the front housing plate and rear housing plate.

Figure 4D:
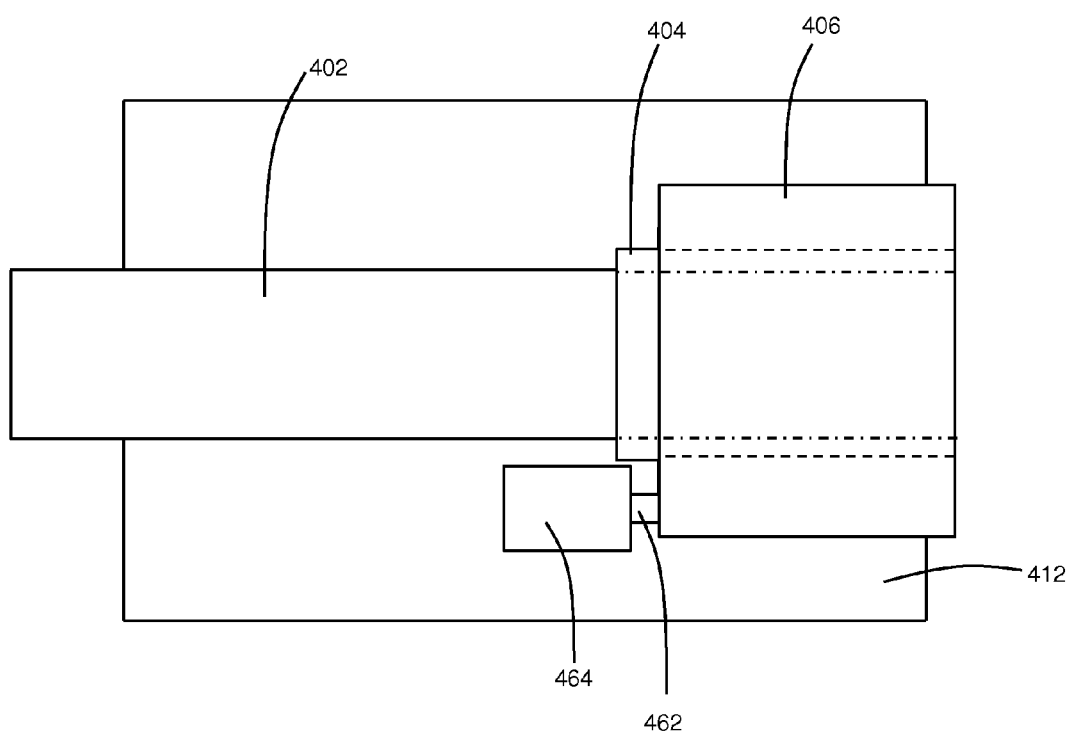
FIG. 4D shows an illustrative heat shield limit switch assembly.

FIG. 4D shows a heat shield limit switch assembly. In some embodiments, when heat shield 406 is inserted into the vaporizer device housing, plunger 462 of limit switch 464 detects whether the heat shield has been fully deployed around the outer transparent insulating tube 404. The limit switch is mounted on PCB 412. When the heat shield is fully deployed, heat shield 406 depresses plunger 462 of limit switch 464 such that a circuit is completed. The device processor monitors the signal received from the limit switch and prevents operation of the heat source if the switch has not been activated.

Figure 5A:
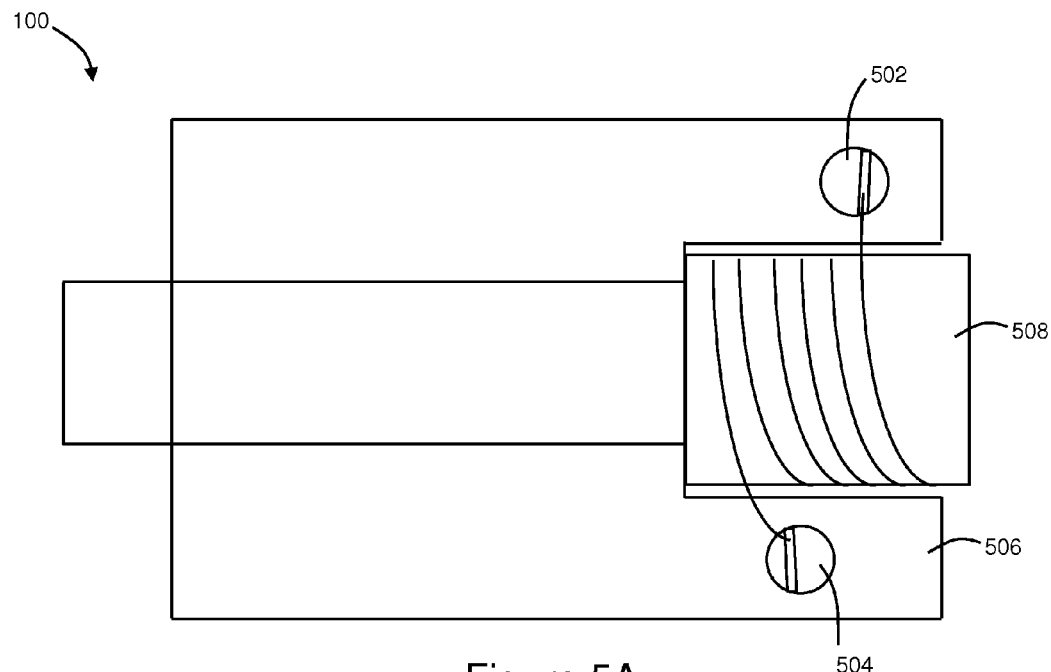
FIG. 5A shows a top view of an illustrative resistance wire assembly of the portable vaporizer.
Figure 5B:
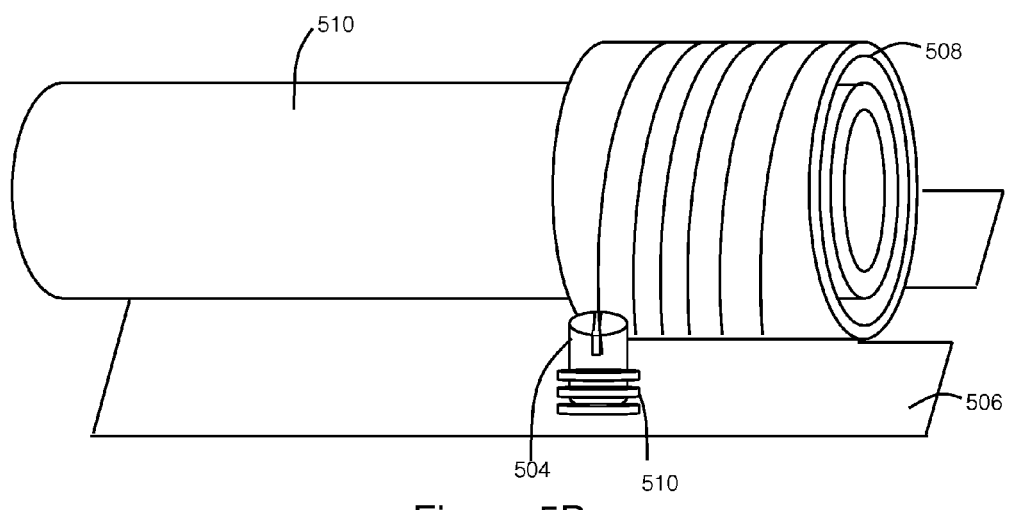
FIG. 5B shows a perspective view of an illustrative resistance wire assembly of the portable vaporizer.

Referring now to FIGS. 5A-5B, a resistance wire assembly of the portable vaporizing device is shown in a top view and a perspective view, respectively. Wire terminals 502 and 504 are coupled to PCB 506. Resistance wire 508 is connected to wire terminals 502 and 504. The resistance wire is preferably a high-resistivity alloy wire such as a nichrome wire. Power is directed from a power source such as a battery to the resistance wire via the wire terminals. The wire terminals may have heat dissipating features such as the fins 510 shown on wire terminal 504 in FIG. 5B. The resistance wire is coiled around outer transparent insulating tube 508. In the illustrative embodiment, the resistance wire is coiled in four to ten turns, e.g. six turns, around the outer transparent insulating tube. The interior surface of the vaporizer housing is preferably polished, with the polished surface increasing the reflectivity of the housing interior surface such that the infrared emissions of the resistance wire that reach the housing interior surface are reflected back toward the transparent insulating tubes.

When power is provided to the resistance wire, the resistance wire emits electromagnetic waves, for example, light in the infrared range. The infrared energy causes the vaporization of the vaporizable matter. The vaporizable matter is vaporized through radiant heating from the infrared energy. In some embodiments, the heating element of the portable vaporizer is another electromagnetic wave source, such as an ultraviolet emitter.

The inner transparent insulating tube 510 may be rotatable relative to outer transparent insulating tube 508, such that vaporizable matter contained within inner transparent insulating tube is agitated and mixed, thereby increasing the exposure of the vaporizable matter surfaces to the device heat source.

Figure 6:
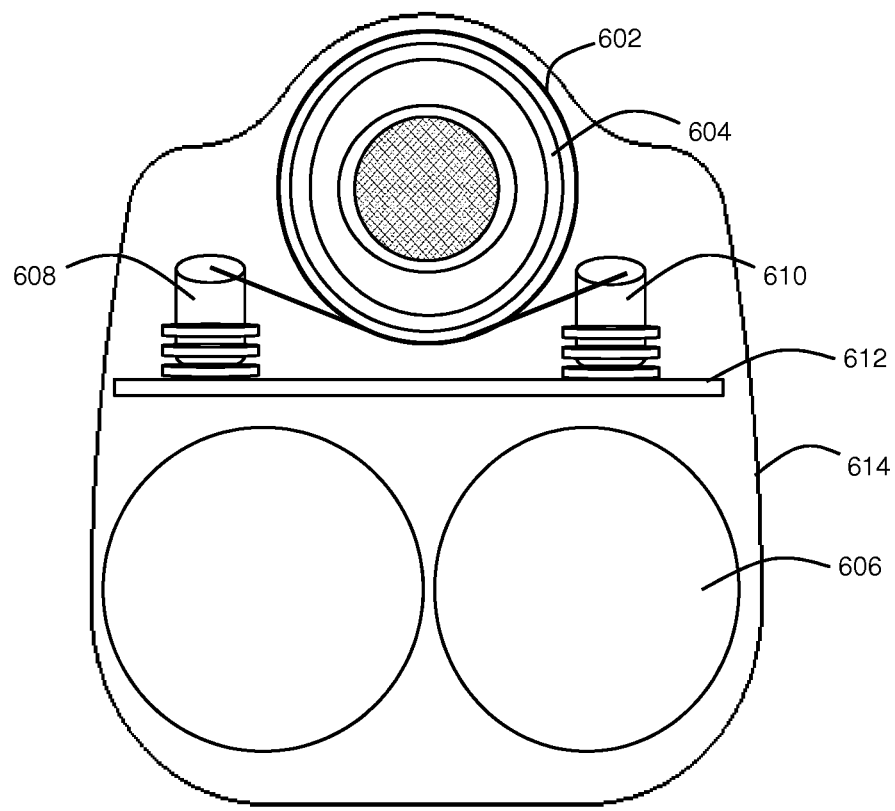
FIG. 6 is an illustrative cross-sectional view of the portable vaporizer.

Referring to FIG. 6, the portable vaporizing device is shown in cross section. Resistance wire 602 is shown wound around outer transparent insulating tube 604. The resistance wire preferably does not contact the outer transparent insulating tube or the vaporizer housing 614. The resistance wire receives power from batteries 606 via wire terminals 608 and 610. A processor coupled to PCB 612 directs the flow of power from the batteries to the wire terminals.

Referring to FIG. 7, a schematic diagram 700 of a control system for a portable vaporizing device is shown. When the vaporizer is powered on, processor 702 determines whether heat shield limit switch 704 is activated. The processor may be a microcontroller. In some embodiments, the processor is a field programmable gate array that may be reprogrammed via the data port 210 shown in FIG. 2A. One or more LEDs 708 may be lit when the vaporizer is powered on.

If the limit switch is activated, indicating that the heat shield is fully inserted into the vaporizer housing, the processor directs power from the power source to the wire terminal 702. In some embodiments, power is transferred from batteries located within the housing to a pair of wire terminals, as shown in FIG. 6. The processor receives a signal from a temperature sensor such as thermistor 706. Thermistor 706 is operatively coupled to the PCB and is preferably located below the centerline of the inner transparent insulating tube.

The amount of power delivered to the wire terminals may be reduced after an initial warm up phase. For example, the processor may initially power the resistance wire at an initial power level, for example, a power level in the range of 20 to 50 watts. In an illustrative embodiment, the initial power level is 30 watts. When the temperature as measured by the temperature sensor reaches a target temperature level, the processor may reduce the power delivered to the resistance wire to a secondary power level, such as 10 watts. The target temperature level may be the vaporization temperature of the vaporizable matter to be used in the vaporizer. In an alternative embodiment, the processor may reduce the power level from an initial power level to a secondary power level when a preset period of time corresponding to an initial power level has elapsed. In some embodiments, the processor may reduce the power to a third power level after a preset period of time corresponding to a secondary power level has elapsed. The processor may also be configured to power down the device after a preset maximum period of device powered-on time has elapsed.

In some embodiments, if the temperature as detected by the temperature sensor has reached a target temperature, the processor sends an instruction to the LED 708 to blink. Alternatively, the LEDs may be instructed to blink when a preset period of time during which the resistance wire emitted energy elapsed. The blinking LEDs indicate that the vaporization of the vaporizable matter has occurred and that the user may inhale the vapor from the inner transparent insulating tube. If the temperature as measured by the temperature sensor exceeds a threshold level, the processor may cease the delivery of power from the power source to the wire terminal until the temperature drops below the threshold level or until the temperature declines to a second threshold level.

The control system also comprises memory 712. The memory may be part of the processor. Alternatively, the memory may be a separate component of the control system. The memory stores instructions used by the processor to control the heating element. The memory may also store information about the state of the device, for example, whether the heat shield has been removed from the device as detected by the limit switch.

Referring now to FIG. 8 there is shown an illustrative flowchart 800 for controlling a portable vaporizer according to one embodiment of the invention. The method begins at decision diamond 802, at which it is determined by the processor whether the heat shield limit switch is activated. If the heat shield limit switch is activated, indicating that the heat shield is fully inserted into the vaporizer housing, power is delivered to the wire terminals at a first power level, as indicated at block 804. The method proceeds to decision diamond 806, at which it is determined whether a target temperature has been reached. In one illustrative embodiment, the processor queries a temperature sensor to determine whether the target temperature has been reached. When a target temperature has been reached, power is delivered to the resistance wire at a second power level, as indicated at block 808. The method then proceeds to decision diamond 810 where it is determined whether the time the device has been powered on exceeds a threshold time. If the threshold time has been exceeded, the supply of power to the wire terminals is discontinued as indicated at block 812.

In some embodiments, the processor tracks in memory the number of times the device has been powered on since the vaporizable matter was last changed, as indicated by tracking whether the heat shield has been removed. If the number exceeds a threshold number, the processor may prevent the delivery of power to the resistance wire until the heat shield is removed.

Referring to FIG. 9, an illustrative signal profile for a portable vaporizer is shown. When the device is powered on, if the heat shield limit switch is activated, the heating element receives power. In the embodiment illustrated in FIG. 9, the amount of power provided to the heating element increases to 30 W over the first four seconds that the device is on. The amount of power provided to the heating element then decreases to 20 W from 4 seconds until 7 seconds and holds steady at 20 W from 7 seconds until 11 seconds. The amount of power provided to the heating element decreases to 10 W from 11 seconds to 12 seconds and holds steady at 10 W from 12 seconds to 15 seconds. At 15 seconds, the device powers down automatically. The heating element structure and emissions produced by the structure change over time as power is applied to the element. Thus the power required to maintain an optimal heat for vaporization changes over time. A complex signal profile such as the one shown in FIG. 9 advantageously allows optimal heating of the vaporizable matter to produce vaporization over the entirety of the period of time during which the heating element is on.

In some embodiments, a first signal profile is applied for a first vaporization period and one or more different signal profiles are applied for subsequent vaporization periods. In a first vaporization period, the power is delivered to the heating element, for example, according to the signal profile shown in FIG. 9, until a first time period has elapsed. The device is automatically powered down by the processor when the first time period, e.g. 15 seconds, has elapsed. When the device is next powered on, vaporizer processor 702 queries the memory 712 to determine whether the removable heat shield has been removed since the last time the device was powered on. If the heat shield has not been removed, the vaporizer determines that the same vaporizable matter is present in the vaporization chamber as was present the last time the device was powered on. Because the vaporizable matter has been changed by the vaporization that occurred during the first vaporization period, a second signal profile may be optimal for the second vaporization of the same vaporizable matter. Thus, a second signal profile, third signal profile, etc. that differ from the first signal profile may be used during subsequent vaporization periods.

The apparatus, systems and methods described above are further related to a drug delivery system that converts active compounds adsorbed onto a binder into a gas phase with minimal inspiratory flow rate requirements.

The illustrative active compound is salicylic acid, which is similar to aspirin. Salicylic acid has a melting point of 159° C. and boiling point of 211° C. When ingested orally, one of the side effects of aspirin is to increase the risk of gastrointestinal bleeding; coated formulations of aspirin do not appear have any effect. Additionally, combining aspirin with non-steroidal anti-inflammatory medicines has been shown to increase the risk of gastrointestinal bleeding. Furthermore, combining aspirin with clopidogrel or warfarin also increases the risk of upper gastrointestinal bleeding.

The illustrative active compound salicylic acid is adsorbed on the surface of the binder. By way of example, the illustrative active compound is in a concentrated aqueous solution such as ethanol and is then applied to the binder. The mixture is then heated to a temperature of 80° C. for the appropriate amount of time to dry the mixture of the active compound and binder.

By way of example and not of limitation, the illustrative binder(s) has a relatively high melting point when compared to the melting point of the active ingredient. For example, calcium carbonate and magnesium carbonate have relatively high melting points, i.e. greater than 500° C.

In the illustrative embodiment, a tablet composed of the binder and the active ingredient, e.g. salicylic acid, is crushed to increase the surface area for the volatilization of the salicylic acid. The crushed tablet may be composed a large granules, powder, or the combination thereof. The tablet is crushed to increase the surface area for the volatilization.

The crushed salicylic acid tablet is then placed in the vaporization chamber of the illustrative quartz tube.

The electrical operating parameters for the tablet have either been preloaded or are downloaded to the vaporization device that controls the heating of the vaporization chamber.

In a broad embodiment, the vaporization chamber is heated to a temperature range from approximately 159° C.-211° C., i.e. the melting point to the boiling point of salicylic acid. In a narrower embodiment, the vaporization chamber is heated to a temperature range from 170° C.-210° C. In an even narrower embodiment, the vaporization chamber is heated to a temperature ranging from 190° C.-205° C.

The vaporizer is powered on and the resistance coils are activated according to the electrical operating parameters that heat the vaporization chamber. The active ingredients in the chamber then migrate to a gas phase. In some embodiments, one or more LEDs 708 flash when the temperature as indicated by the temperature sensor 706 has reached the target temperature for consuming the active ingredient. The patient then consumes the active ingredient by inhaling.

The patient may then proceed to turn the inner insulated tube 402 and the crushed tablet is further radiated by the resistance coil according to the electrical operating parameters.

The appropriate electrical operating parameters associated with the other crushed tablet may be written to the processor 702 via charging/data port 210. The apparatus, systems and methods operates in a manner similar to the method described above.

The apparatus, system and method do not require a high inspiratory flow rate, and additionally reduce the risk of gastrointestinal bleeding, lack pressurized cylinders, and allow air flow into the sublimation chamber, thereby overcoming the challenges associated with Dry Powder Inhalers. Additionally, the volatilization of salicylic acid may have additional applications such as for the treatment of bronchitis.

It is to be understood that the detailed description of illustrative embodiments are provided for illustrative purposes. The scope of the claims is not limited to these specific embodiments or examples. Therefore, various process limitations, elements, details, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. An electronic device for volatilizing organic-compounds associated with a solid material, the electronic device comprising:
   a transparent tube that allows for infrared electromagnetic transmittance to pass through the transparent tube, the transparent tube including an inner wall, an outer wall, an open end, a distal end and a vaporization chamber that interfaces with the inner wall;
   a first screen disposed on a first side of the vaporization chamber;
   a removable second screen disposed on an opposite side of the vaporization chamber, wherein the solid material is received between the first screen and the removable second screen;
   an infrared heating element surrounding the outer wall of the portion of the vaporization chamber, wherein the infrared heating element includes a coiled resistance wire that surrounds the outer wall of the transparent tube;
   a settings profile that includes a first wattage setting and a first timer setting for the heating element, wherein the heating element volatilizes at least one compound corresponding to the solid material in the vaporization chamber by transmitting electromagnetic energy from the coiled resistance wire through the transparent tube and to the vaporization chamber;
   a memory that stores the settings profile;
   a processor operatively coupled to the memory module that controls the heating element according to the settings profile;
   a power supply controlled by the processor;
   a user switch communicatively coupled to the processor, wherein the user switch activates the heating element according to the settings profile to volatilize the active compound in the chamber; and wherein the volatilized compound is configured to travel from the distal end of the transparent tube having the vaporization chamber to the open end of the transparent tube.

2. The electronic device of claim 1 wherein the coiled resistance wire is configured to emit infrared energy at an electromagnetic frequency range between 1,000 nm-20,000 nm.

3. The electronic device of claim 2 wherein the processor is configured to initially power the coiled resistance wire to a target temperature and a temperature sensor that is used to determined when the target temperature has been reached.

4. The electronic device of claim 3 wherein the processor is configured to reduce the power delivered to the coiled resistance wire to a secondary power level after the target temperature has been reached.

5. The electronic device of claim 2 wherein the electronic device is configured to be powered a plurality of times.

6. The electronic device of claim 1 further comprising a first setting profile configured to provide a high initial power and then configured to reduce the power setting over a period of time.

7. The electronic device of claim 1 further comprising a plurality of settings profile, in which a first settings profile is associated with a first vaporization period and a second setting profile is associated with a second vaporization period, wherein the first vaporization period precedes a second vaporization period.

8. A method of volatilizing organic compounds associated with a solid material with an electronic device, the method comprising:
    enabling a vaporization chamber to receive at least one organic compound, wherein the vaporization chamber occupies a portion of a transparent tube that allows for infrared electromagnetic transmittance to pass through the transparent tube, the transparent tube having an inner wall, an outer wall, an open end, a distal end and the vaporization chamber on the distal end interfacing with the inner wall;
    receiving the solid material between a first screen and a removable second screen, wherein the first screen is disposed on a first side of the vaporization chamber and the removable second screen is disposed on an opposite side of the vaporization chamber;
    surrounding the outer wall of the portion of the transparent tube that houses the vaporization chamber with an infrared heating element, wherein the infrared heating element includes a coiled resistance wire that surrounds the outer wall of the transparent tube;
    storing a settings profile in a memory, wherein the settings profile includes a first wattage setting and a first timer setting for the heating element that surrounds the vaporization chamber of the transparent tube;
    activating the heating element with a user switch;
    initiating the settings profile;
    powering the activation of the heating element;
    controlling the activation of the heating element according to the settings profile; and
    volatilizing at least one compound corresponding to the solid material in the volatilization chamber by transmitting electromagnetic energy and heat from the coiled resistance wire through the transparent tube and to the vaporization chamber, wherein the volatilized compound travels from the distal end of the transparent tube having the vaporization chamber to the open end of the transparent tube.

9. The method of claim 8 wherein the coiled resistance wire emits infrared energy at an electromagnetic frequency range between 1000 nm-20,000 nm.

10. The method of claim 9 further comprising enabling a processor to initially power the coiled resistance wire to a target temperature and a temperature sensor that is used to determine when the target temperature has been reached.

11. The method of claim 10 further comprising enabling the processor to reduce the power delivered to the coiled resistance wire to a secondary power level after the target temperature has been reached.

12. The method of claim 9 further comprising powering the electronic device a plurality of times.

13. The method of claim 8 further comprising heating the organic compound with a first settings profile that provides a high initial power and then reducing the power setting over a time period.

14. The method of claim 8 further comprising providing a plurality of settings profiles, in which the first settings profile is associated with a first vaporization period and a second settings profile is associated with a second vaporization period, wherein the first vaporization period precedes a second vaporization period.

15. An electronic device for volatilizing compounds associated with a solid material, the electronic device comprising:
    a transparent tube that allows for infrared electromagnetic transmittance to pass through the transparent tube, wherein the transparent tube has an inner wall an outer wall, an open end, a distal end and a vaporization chamber on the distal end that interfaces with the inner wall;
    a first screen disposed on a first side of the vaporization chamber;
    a removable second screen disposed on an opposite side of the vaporization chamber, wherein the solid material is received between the first screen and the removable second screen;
    an infrared heating element surrounding the outer wall of the portion of the vaporization chamber, wherein the infrared heating element includes a coiled resistance wire that surrounds the outer wall of the transparent tube;
    a settings profile that includes a first wattage setting and a first timer setting for the heating element, wherein the heating element volatilizes at least one compound corresponding to the solid material in the vaporization chamber by transmitting electromagnetic energy from the coiled resistance wire though the transparent tube and to the vaporization chamber; and
    wherein the volatilized compound is configured to travel from the distal end of the transparent tube having the vaporization chamber to the open end of the transparent tube.

16. The electronic device of claim 15 further comprising a processor that initially powers the coiled resistance wire to a target temperature and a temperature sensor that is used to determined when the target temperature has been reached.

17. The electronic device of claim 16 wherein the processor reduces the power delivered to the coiled resistance wire to a secondary power level after the target temperature has been reached.

18. The electronic device of claim 16 wherein the electronic device is powered a plurality of times.

19. The electronic device of claim 15 further comprising a first setting profile that provides a high initial power and then reducing the power setting over a period of time.

20. The electronic device of claim 15 further comprising a plurality of settings profile, in which the first settings profile is associated with a first vaporization period and a second setting profile is associated with a second vaporization period, wherein the first vaporization period precedes a second vaporization period.

* * * * *